United States Patent
Cahill et al.

(10) Patent No.: US 9,131,962 B2
(45) Date of Patent: Sep. 15, 2015

(54) BONE SCREW ASSEMBLY

(75) Inventors: Douglas Cahill, Lititz, PA (US);
Andrew Lott, Villanova, PA (US);
Khiem Pham, Chalfont, PA (US);
Edward Karpowicz, Swedesboro, NJ (US)

(73) Assignee: GLOBUS MEDICAL, INC., Audubon, PA (US)

( * ) Notice: Subject to any disclaimer, the term of this patent is extended or adjusted under 35 U.S.C. 154(b) by 238 days.

(21) Appl. No.: 13/114,803

(22) Filed: May 24, 2011

(65) Prior Publication Data
US 2012/0303063 A1   Nov. 29, 2012

(51) Int. Cl.
*A61B 17/70* (2006.01)

(52) U.S. Cl.
CPC ......... *A61B 17/7037* (2013.01); *A61B 17/7032* (2013.01); *A61B 17/7041* (2013.01)

(58) Field of Classification Search
CPC .............. A61B 17/70; A61B 17/7001; A61B 17/7032–17/7046
USPC ................................................ 606/246–278
See application file for complete search history.

(56) References Cited

U.S. PATENT DOCUMENTS

| | | | |
|---|---|---|---|
| 4,950,269 A | 8/1990 | Gaines, Jr. | |
| 5,084,048 A | 1/1992 | Jacob | |
| 5,466,237 A | 11/1995 | Byrd, III | |
| 5,474,555 A | 12/1995 | Puno | |
| 5,672,176 A | 9/1997 | Biedermann | |
| 5,797,911 A | 8/1998 | Sherman | |
| 5,817,094 A | 10/1998 | Errico | |
| 5,863,293 A | 1/1999 | Richelsoph | |
| 5,879,350 A | 3/1999 | Sherman | |
| 5,882,350 A | 3/1999 | Ralph | |
| 5,885,286 A | 3/1999 | Sherman | |
| 5,891,145 A | 4/1999 | Morrison | |
| 6,063,090 A | 5/2000 | Schlapfer | |
| 6,074,391 A | 6/2000 | Metz-stavenhagen | |
| 6,077,262 A | 6/2000 | Schlapfer | |
| 6,090,111 A | 7/2000 | Nichols | |
| 6,113,601 A | 9/2000 | Tatar | |
| 6,187,005 B1 | 2/2001 | Brace | |
| 6,302,888 B1 | 10/2001 | Mellinger | |
| 6,371,957 B1 | 4/2002 | Amrein | |
| 6,475,218 B2 | 11/2002 | Gournay | |
| 6,565,566 B1 | 5/2003 | Wagner | |

(Continued)

FOREIGN PATENT DOCUMENTS

WO   WO 2009014540 A1 *  1/2009

*Primary Examiner* — Jerry Cumberledge
*Assistant Examiner* — Nicholas Plionis

(57) ABSTRACT

Spine stabilization systems are disclosed. One spine stabilization system includes a bone screw assembly including a coupling member and a screw member received therein. The coupling member includes a pair of extension elements that form a pair of slots. The slots include bottom angled surfaces. An angled wedge member having a substantially horizontal bottom surface and an angled top surface is delivered on top of the screw member within the coupling member. A rod member can be delivered down the coupling member such that it rests on the slots and on top of the angled wedge member. A locking assembly comprising a cap member and set screw can be delivered down the coupling member to secure the rod member to the coupling member. The rod member and locking assembly components can be delivered through a single incision and at a same or similar angle as the screw member during surgery.

16 Claims, 9 Drawing Sheets

(56) References Cited

U.S. PATENT DOCUMENTS

| | | |
|---|---|---|
| 6,755,829 B1 | 6/2004 | Bono |
| 6,786,903 B2 | 9/2004 | Lin |
| 6,843,791 B2 | 1/2005 | Serhan |
| 6,858,030 B2 | 2/2005 | Martin |
| 6,869,433 B2 | 3/2005 | Glascott |
| 6,893,443 B2 | 5/2005 | Frigg |
| 6,974,460 B2 * | 12/2005 | Carbone et al. ............... 606/305 |
| 7,081,117 B2 | 7/2006 | Bono |
| 7,128,743 B2 | 10/2006 | Metz-stavenhagen |
| 7,141,051 B2 | 11/2006 | Janowski |
| 7,338,491 B2 | 3/2008 | Baker |
| 7,491,218 B2 | 2/2009 | Landry |
| 7,559,943 B2 | 7/2009 | Mujwid |
| 7,678,137 B2 | 3/2010 | Butler |
| 7,722,651 B2 | 5/2010 | Kwak |
| 7,744,636 B2 | 6/2010 | Richelsoph |
| 7,766,946 B2 | 8/2010 | Bailly |
| 7,799,054 B2 | 9/2010 | Kwak |
| 2002/0010467 A1 | 1/2002 | Cooper |
| 2002/0045899 A1 | 4/2002 | Errico |
| 2002/0120272 A1 | 8/2002 | Yuan |
| 2002/0151900 A1 | 10/2002 | Glascott |
| 2003/0125741 A1 | 7/2003 | Biedermann |
| 2004/0097933 A1 | 5/2004 | Lourdel |
| 2004/0158247 A1 | 8/2004 | Sitiso |
| 2004/0172022 A1 | 9/2004 | Landry |
| 2005/0049588 A1 | 3/2005 | Jackson |
| 2005/0055026 A1 | 3/2005 | Biedermann |
| 2005/0080415 A1 * | 4/2005 | Keyer et al. .................... 606/61 |
| 2005/0228385 A1 * | 10/2005 | Iott et al. ........................ 606/61 |
| 2005/0277919 A1 | 12/2005 | Slivka |
| 2006/0111715 A1 | 5/2006 | Jackson |
| 2006/0129149 A1 | 6/2006 | Iott |
| 2006/0142761 A1 | 6/2006 | Landry |
| 2006/0195098 A1 * | 8/2006 | Schumacher .................. 606/61 |
| 2008/0077143 A1 | 3/2008 | Shluzas |
| 2008/0294202 A1 | 11/2008 | Peterson et al. |
| 2010/0016898 A1 | 1/2010 | Shluzas |
| 2010/0234891 A1 | 9/2010 | Freeman |

* cited by examiner

BONE SCREW ASSEMBLY

FIELD OF THE INVENTION

The present application generally relates to a spinal stabilization system including a bone screw assembly, and in particular, a polyaxial screw assembly incorporating an angled wedge member.

BACKGROUND OF THE INVENTION

Many surgical procedures require securing an implant to bone, for example, to vertebrae along the spine. Orthopedic fixation devices are frequently coupled to bone by the use of fasteners such as screws, threaded bolts, or pins. For example, a rod implant can be operatively coupled to bone with the assistance of one or more bone screw assemblies designed to receive the rod implant. The rod implant can be secured across one or more vertebrae to assist in bone stabilization. Each of the bone screw assemblies can include a locking assembly such as a cap and set screw to secure the rod implant therein.

The bone screw assemblies and implants can be delivered minimally invasively through one or more incisions. In order to insert the bone screw assemblies and implants, the one or more incisions may need to be expanded in size. Expanding the size of an incision can detrimentally increase the amount of trauma to a patient and can extend the amount of time for healing. It also increases the operation time by requiring an extra step to be performed by a surgeon.

Accordingly, it is desirable to provide spinal stabilization systems that reduce the need to expand an incision during surgery, or at least reduce the size of expansion.

SUMMARY OF THE INVENTION

Spine stabilization systems are provided. In some embodiments, a bone stabilization system comprises a coupling member; a screw member configured to be received in the coupling member; a wedge member configured to be received in the coupling member and positioned on top of the screw member, wherein the wedge member includes a bottom surface and a top surface that is non-parallel to the bottom surface; a rod implant configured to be received in the coupling member; and a locking assembly configured to compress and secure the rod implant within the coupling member.

In other embodiments, a bone stabilization system comprises a coupling member including a pair of extension elements and a pair of angled slots formed therebetween, wherein the angled slots include angled contact surfaces; a screw member configured to be received in the coupling member; a wedge member configured to be received in the coupling member and positioned on top of the screw member; a rod implant configured to be received in the coupling member and positioned on top of the angled contact surfaces; and a locking assembly configured to compress and secure the rod implant within the coupling member.

In other embodiments, a bone stabilization system comprises a coupling member including a pair of extension elements, wherein the pair of extension elements form slots, wherein the bottom of the slots include angled contact surfaces for contacting a rod member delivered in the coupling member, and wherein the coupling member includes one or more inner bumper elements; a screw member including a head and a threaded shaft, wherein the screw member is configured to be received in the coupling member; a coupling body component including one or more slits, wherein the coupling body component is configured to extend over a portion of the head of the screw member to assist in securing the screw member to the coupling member; an angled wedge member configured to be received in the coupling member on top of the screw member, the angled wedge member including a substantially horizontal bottom surface and an angled top surface that is non-parallel to the bottom surface; a rod member receivable in the slots of the coupling member, wherein the rod member is configured to contact the angled top surface of the angled wedge member; and a locking assembly comprising a cap member and a set screw, the set screw having an angled bottom surface that is substantially at the same angle as the angled top surface of the angled wedge member, wherein the locking assembly is configured to be delivered down the coupling member to apply a compressive force that secured a rod member within the coupling member.

DETAILED DESCRIPTION OF THE ILLUSTRATED EMBODIMENTS

Figure 1:
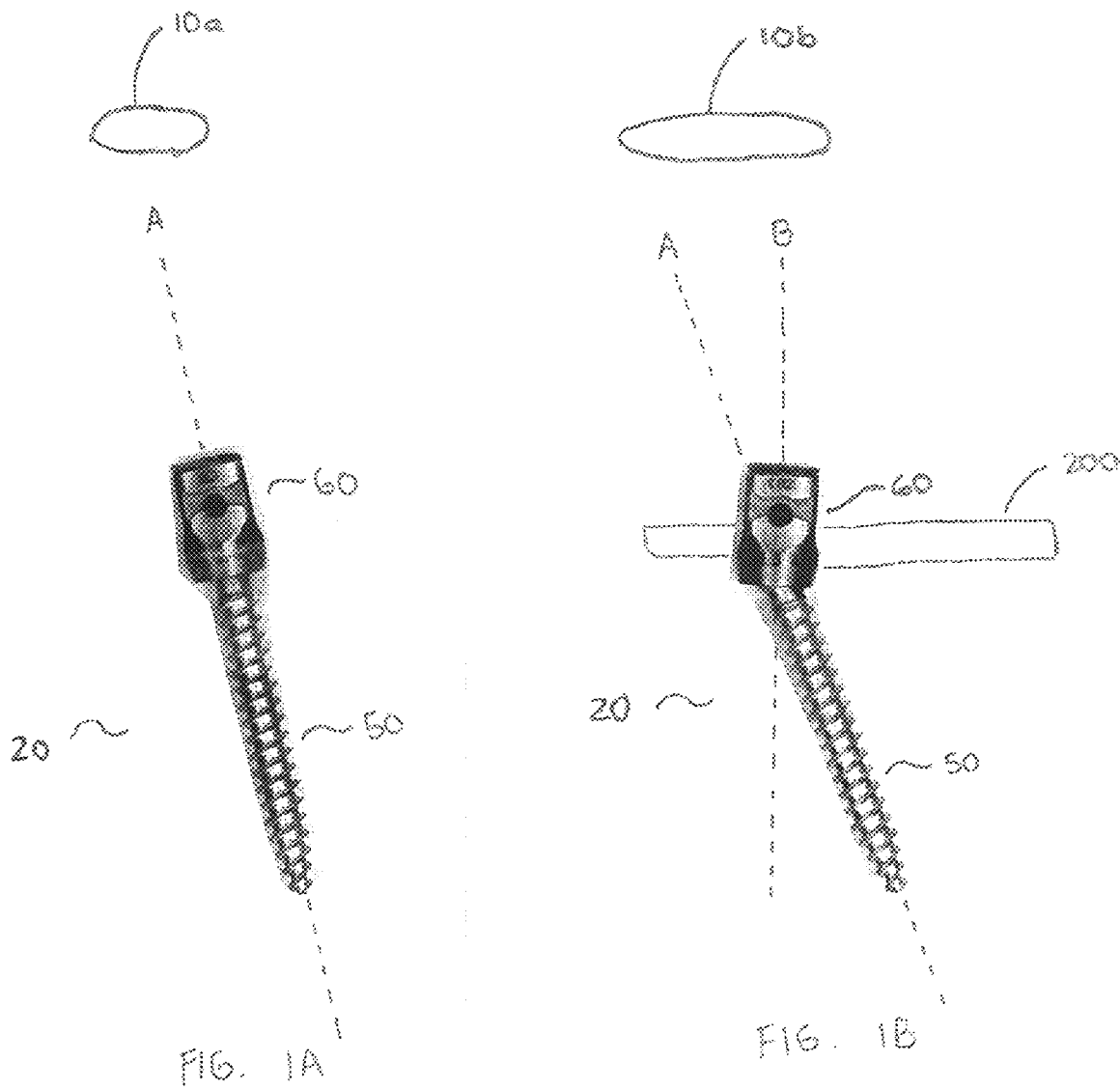
FIG. 1A is a side view of a bone screw assembly.
FIG. 1B is a side view of the bone screw assembly of FIG. 1A with the angle of the coupling member adjusted.

Detailed embodiments of the invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present application generally relates to a bone stabilization system including an improved bone screw assembly, and in particular, a polyaxial screw assembly incorporating an angled wedge member. The angled wedge member, which includes a slanted or angled surface, advantageously allows for an implant and/or locking assembly to be delivered into a desired position at a same or similar angle as a screw member through an incision, thereby reducing the need to expand the size of an incision during surgery.

FIGS. 1A and 1B are side views of a conventional bone screw assembly, and illustrate the difficulties faced by such assemblies. The bone screw assembly 20 includes a screw member 50 having a head and a shaft that is operatively attached to a coupling member 60. The coupling member 60 can receive an implant, such as rod member 200 (shown in FIG. 1B). The coupling member 60 can be oriented in various angles relative to the screw member 50, thereby forming a polyaxial screw assembly.

As shown in FIG. 1A, the bone screw assembly 20 includes a screw member pre-attached to a coupling member 60. The bone screw assembly 20 can be inserted through an incision 10a, whereby the screw member 50 can be delivered along an A-axis (shown running along a longitudinal axis of the screw member 50). The screw member 50 can then be inserted at an angle into a bone member (not shown). To assist in delivering the bone screw assembly 20, an extension member or sleeve (not shown) can be provided.

As shown in FIG. 1B, an implant, such as a rod member 200, can be delivered and seated in the coupling member 60. To assist in the proper orientation of the rod relative to the spine, the angle of orientation of the coupling member 60 can be adjusted, such that the longitudinal axis of the coupling member is now along a B-axis, as shown in FIG. 1B. In order to secure the rod member 200 in the coupling member 60, a locking assembly (e.g., a cap and set screw) can be advanced down the coupling member to compress and secure the rod member 200 on the seat of the coupling member 60. The rod member and locking assembly would be advanced along the B-axis, which is at a different intersecting angle from the A-axis. Accordingly, in view of the different axis of advancement, the incision 10a would need to be expanded in order to accommodate the advancement of the rod member and locking assembly down the B-axis. The larger incision 10b is illustrated in FIG. 1B. In addition, tissue along the B-axis would need to be cleared and/or removed. Expanding the size of the incision increases the amount of trauma to a patient and increases the time of surgery.

The present application provides an improved bone screw assembly that reduces the need to expand the incision during surgery. By providing an angled wedge member within the coupling member, the orientation of the coupling member can remain substantially the same as when the screw member was delivered through the incision, thereby allowing the rod member and the locking assembly components to be delivered at the same or substantially similar angle as the screw member through the incision. For example, with reference to FIG. 1A, using the improved bone screw assembly would allow the rod member and locking mechanism to be delivered along the A-axis, thereby reducing the need to expand the incision.

Figure 2:
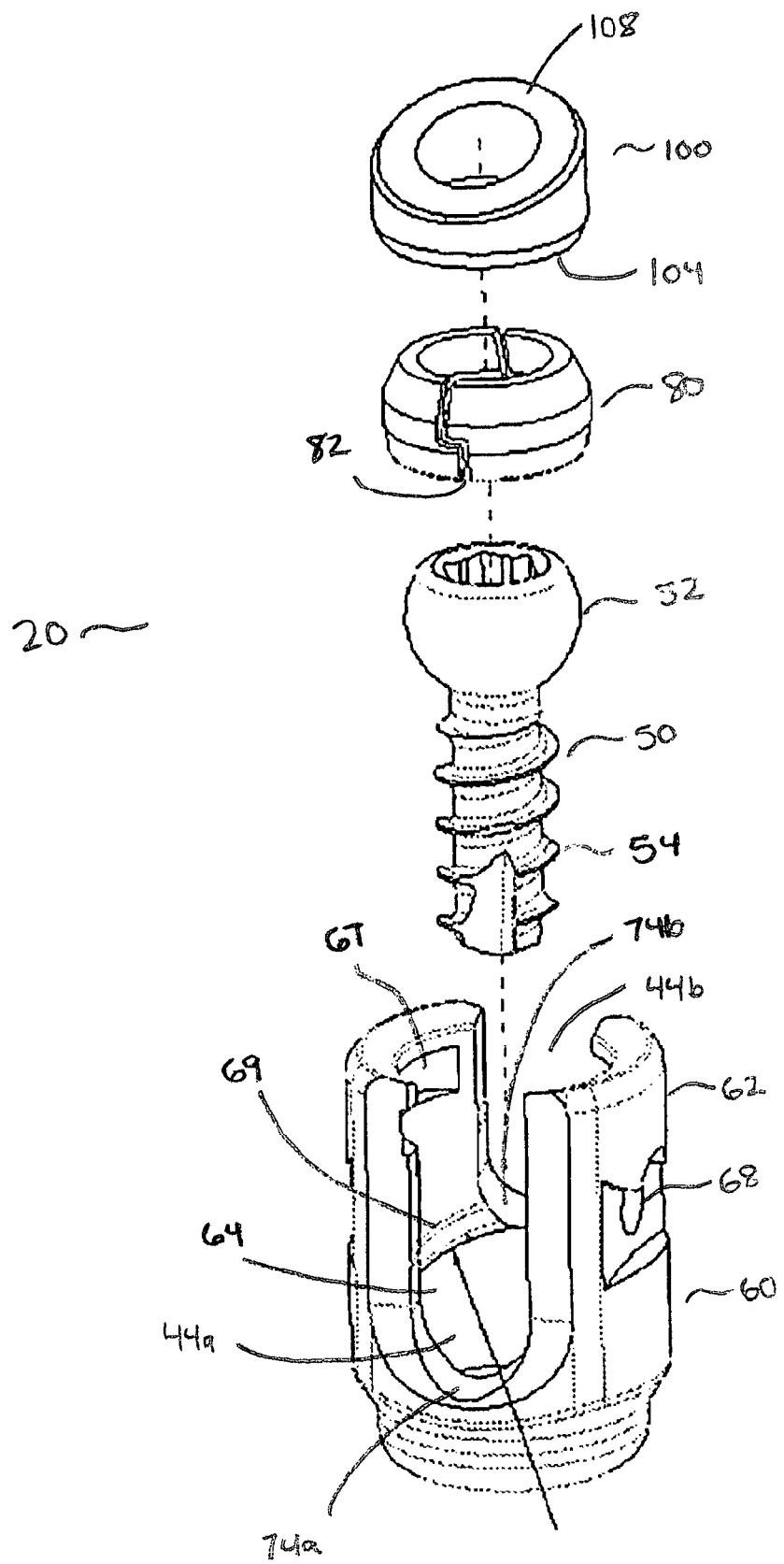
FIG. 2 is an exploded perspective view of a bone screw assembly including an angled wedge member according to some embodiments.
Figure 5:
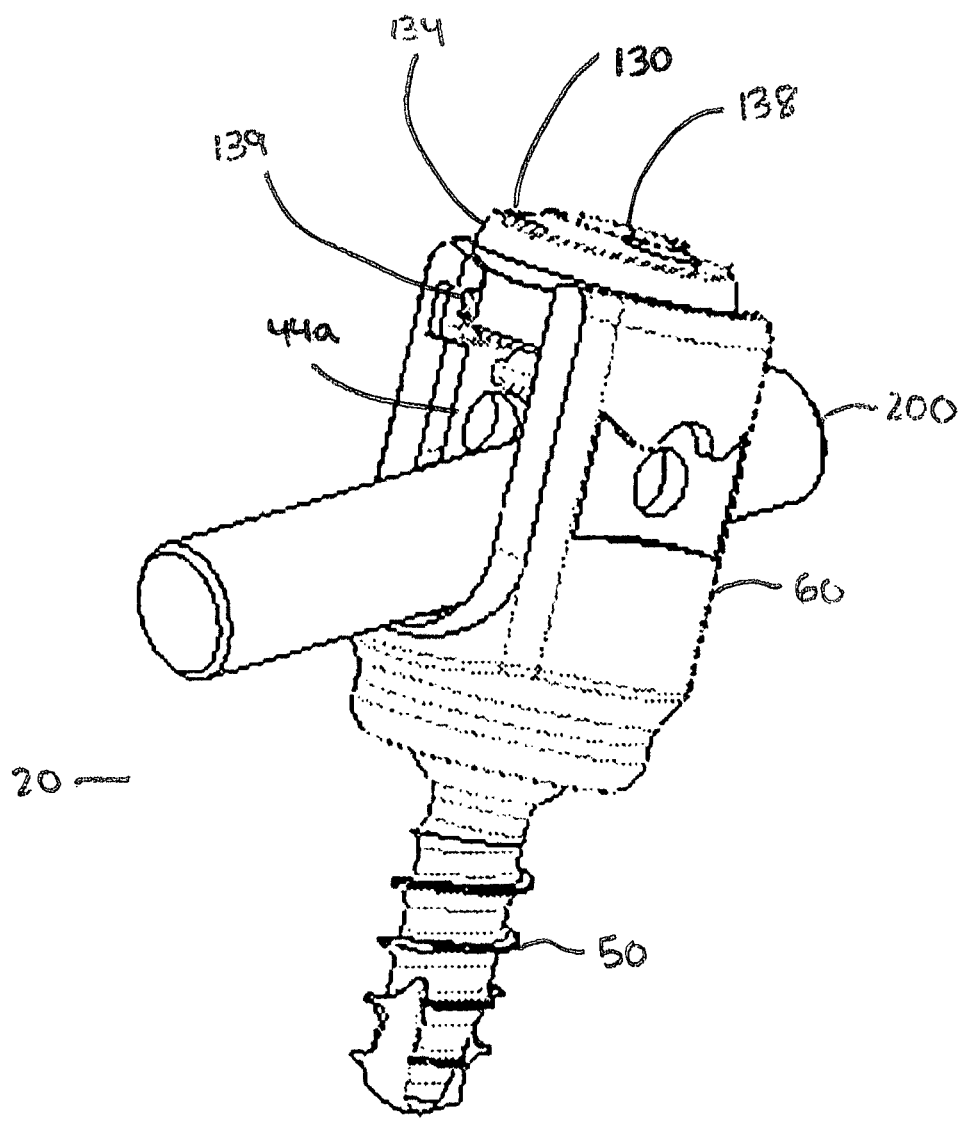
FIG. 5 is a perspective view of a bone screw assembly with locking assembly and implant according to some embodiments.

FIG. 2 is an exploded perspective view of an improved bone screw assembly including an angled wedge member according to some embodiments. The bone screw assembly 20 includes a coupling member 60, a screw member 50, a coupling body component 80 and an angled wedge member 100. The coupling member 60 helps to operatively couple a rod member with the screw member 50, as shown in FIG. 5.

The coupling member 60 includes a pair of extension elements 62, each of which includes an aperture 68 and an inner surface 64. The aperture 68 can be configured to receive a portion of a guiding tool or component (e.g., a tab), such as a guiding sleeve (not shown) that can help to deliver the bone screw assembly to a desired location within a patient. In some embodiments, a bumper element 69 designed to receive and retain a wedge member can be formed in the inner surface 64 of one or both of the extension elements 62. The extension elements 62 can also include a recess or groove 67 for receiving a mateable portion of a locking assembly (as shown in FIG. 5).

Figure 4:
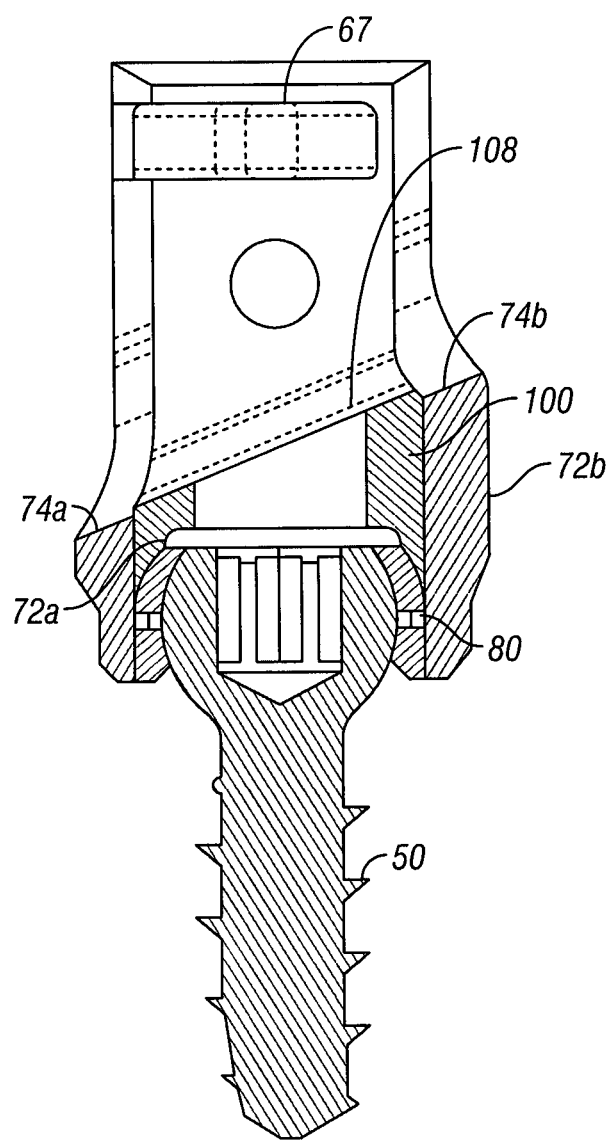
FIG. 4 is a cross-sectional view of a bone screw assembly according to some embodiments.

In some embodiments, the extension elements 62 comprise a pair of arms capable of splaying. The extension elements 62 help to form openings or slots 44a and 44b on opposing sides of the coupling member 60. While the slots are illustrated as substantially U-shaped, slots of other shapes (e.g., rectangular) are also possible. At the bottom of the slots 44a and 44b are angled contact surfaces 74a and 74b (shown in FIGS. 2 and 4) that are designed to contact an implant such as a rod member that is seated within the slots. FIG. 4 illustrates the angled slots 44a and 44b.

Adjacent to the bottom of the angled slots 44a and 44b are exposed lower surfaces 72a and 72b, shown in FIG. 4. In some embodiments, the lower surfaces 72a and 72b are of different height and help to retain the angled wedge member 100 within the coupling member 60. As shown in FIG. 4, the extended lower surface 72b is greater in height than lower surface 72a.

In some embodiments, one or more of the extension elements 62 can include at least one bumper element 69, as shown in FIG. 1. The bumper element 69 can comprise an extended or protruding surface that extends from the inner surface 64 of the coupling member 60. The bumper element 69 can assume a number of shapes, including flat and/or rounded surfaces. In some embodiments, the bumper element 69 comprises one or more nubs positioned intermittently along a portion of the width of the extension element 62, while in other embodiments, the bumper element 69 comprises a protruding shoulder that extends along a substantial portion of the width of the extension element 62. In some embodiments, the bumper element 69 is substantially horizontal (e.g., transverse to an inner surface 64 of an extension element), while in other embodiments, the bumper element 69 is at an angle other than horizontal. For example, in some embodiments, the bumper element 69 can be at an angle of between about 10 and 60 degrees, or between about 15 and 40 degrees relative to a horizontal plane to accommodate the angled wedge member 100. In one embodiment, a bumper element is at about a 20 degree angle relative to a horizontal plane and helps to keep an angled wedge member having a surface of a similar angle in place within the coupling member 60.

In the illustrated embodiment in FIG. 2, each of the extension elements 62 include a bumper element 69 in the form of a protruding shoulder formed along an inner surface of the extension elements. The bumper element 69 is angled relative to a horizontal plane (e.g., a plane transverse to an inner wall of the coupling element) to accommodate the angle surface of the angled wedge member 100. Advantageously, the bumper element 69 helps to retain the angled wedge member 100 within the coupling member 60 and maintain its proper orientation.

When an angled wedge member 100 is positioned within the coupling member 60 (as shown in FIG. 4), the one or more bumper elements 69 advantageously help to prevent spin of the angled wedge member and ensure proper orientation in the coupling member 60. In some embodiments, the bumper element 69 is formed of a material, such as titanium, stainless steel, cobalt-chrome or other metals or metal alloys that advantageously allows for some flexibility when receiving the angled wedge member. In some embodiments, the one or more bumper elements 69 can be formed of the same material as the rest of the coupling member 60. While in some embodiments, the bumper elements 69 are formed separately and attached to the coupling member 60, in other embodiments, the bumper elements 69 are formed as part of the coupling member 60.

In other embodiments, rather than having a bumper element 69 that comprises an extended or protruding surface, the inner surface 64 of the coupling member 60 can include a grooved or recessed portion for receiving a flanged portion of the angled wedge member. Like a protruding bumper element, alternative embodiments that include a grooved or recessed portion in the inner surface of the coupling member can help to retain the angled wedge member in a proper orientation and secure an angled wedge member within the coupling member. In some embodiments, the angled wedge member can include one or more protrusions that mate with the recessed portion of the coupling member 60 to properly align the wedge member within the coupling member. The protrusions advantageously help to provide the angled wedge member with a proper orientation when placed in the coupling member 60.

The screw member 50 includes a head 52 attached to a threaded shaft 54. The coupling body component 80, which includes one or more slits 82, can be placed around the head 52 of the screw member 50. In some embodiments, the coupling body component 80 is comprised of a single member divided by one or more slits 82, while in other embodiments, the coupling body component 80 is comprised of two or more members with one or more slits 82 therebetween. The coupling body component 80 and the screw member 50 can be delivered downwardly into contact with the inner surface 64 of the coupling member 60. The wedge member 100 (discussed further below) can be placed on top of the coupling body element 80. Applying a downward force on the wedge member 100 results in a transmitted force that presses the coupling body component 80 against the inner surface 64 of the coupling member 60. This results in a compressive force on the coupling body component 80 that closes the slits 82 and tightly secures the screw member 50 within the coupling member 60.

The angled wedge member 100 includes a bottom surface 104 and an angled top surface 108 relative to the bottom surface 104. In some embodiments, the bottom surface 104 is substantially horizontal, while the angled top surface 108 is at a non-parallel angle relative to the bottom surface 104. In some embodiments, the angled top surface 108 is at an angle of between about 5 and 50 degrees, or between about 10 and 30 degrees relative to the bottom surface 104. Accordingly, one side of the wedge member 100 is at a greater height than another side of the wedge member 100. When the assembly is assembled, the side of the wedge member 100 that is of greater height can be positioned adjacent to the extended lower surface 72b of the coupling member 60, while the side of the wedge member 100 that is of lesser height can be positioned adjacent to the shorter lower surface 72a, as shown in FIG. 4. The angled wedge member 100 is configured to advantageously orient a rod member in a desired orientation, without having to adjust the angle or orientation of the coupling member 60 relative to the screw member 50. This advantageously reduces the need to expand the size of the incision when inserting the rod member and subsequent locking assembly in a patient, thereby reducing the amount of trauma to the patient.

Figure 3:
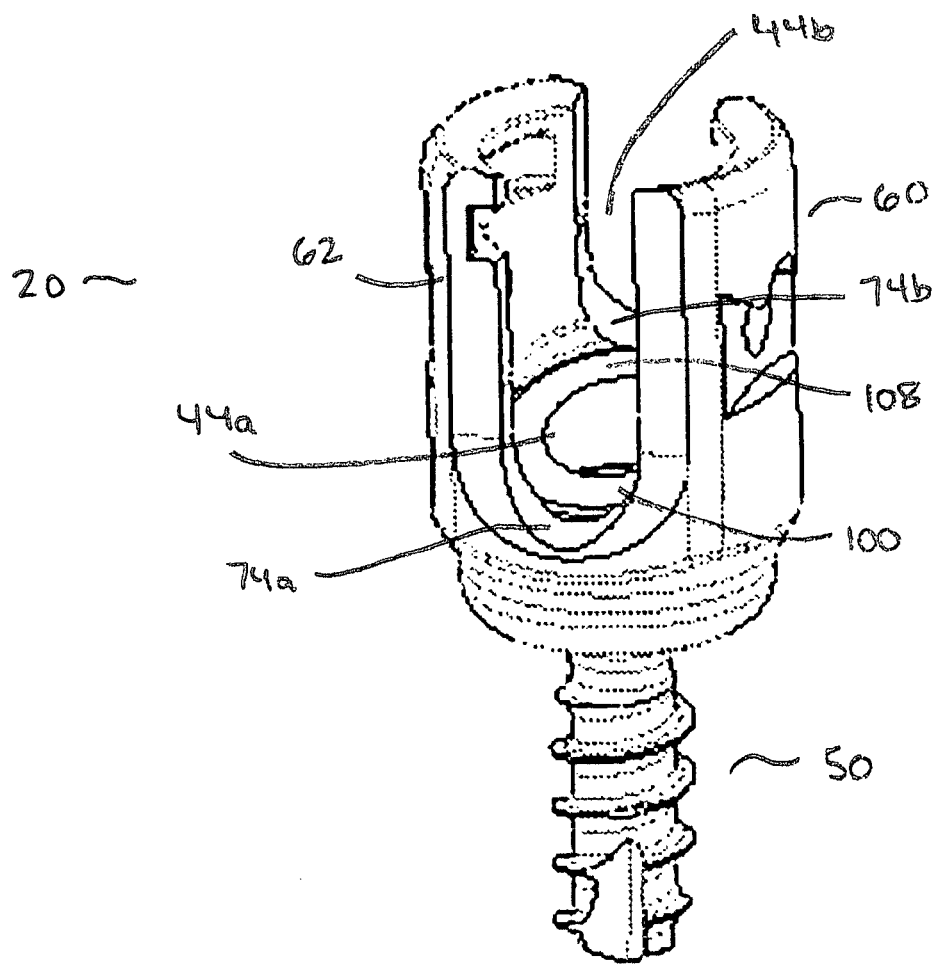
FIG. 3 is a perspective view of a bone screw assembly according to some embodiments.

FIG. 3 is a perspective view of a bone screw assembly according to some embodiments. The bone screw assembly 20 includes a coupling member 60 assembled with a screw member 50, coupling body component (not visible) and an angled wedge member 100. As shown in FIG. 3, the extension elements 62 of the coupling member 60 help to form a pair of angled slots 44a and 44b that are capable of receiving an implant, such as a rod member.

FIG. 4 is a cross-sectional view of a bone screw assembly according to some embodiments. From this perspective, the sloped and angled top surface 108 of the angled wedge member 100 is visible. Also visible are the sloped and angled contact surfaces 74a and 74b of the pair of angled slots 44a and 44b that are configured to receive an implant, such as a rod member. A groove 67 positioned on the inner surface of the extension elements is also illustrated. A locking assembly (discussed in more detail below) can interact with the groove.

FIG. 5 is a perspective view of a bone screw assembly with locking assembly and implant according to some embodiments. An implant 200 in the form of a rod member is received in the angled slots 44a and 44b of the coupling member 60. The rod member rests on top of the angled contact surfaces of the angled slots 44a and 44b. The rod member also rests above an angled wedge member (not shown in the figure) that is placed within the coupling member 60.

Once the rod member is placed in a desired orientation, a locking assembly 130 can be delivered downwardly to secure the rod member in place. In some embodiments, the locking assembly 130 comprises a cap member 134 and a set screw 138, although other locking assemblies are also possible. The cap member 134 can include a mating surface 139 that is designed to secure the cap member 134 to an inner surface of the coupling member 60. A set screw 138 having external threads can be received in the cap member 134. When the set screw 138 is advanced downwardly through the cap member 134, a bottom surface of the set screw 138 can contact the rod member and apply a compressive force, thereby securing the implant in the bone screw assembly. Advantageously, the bone screw assembly is configured such that the implant and the components of the locking assembly can be delivered at the same angle as the screw member, thereby removing or reducing the need to expand the size of the incision. The angled wedge member and/or angled slot helps to properly orient the implant without having to change the orientation of the coupling member relative to the screw member, as shown in FIG. 1B.

Figure 6:
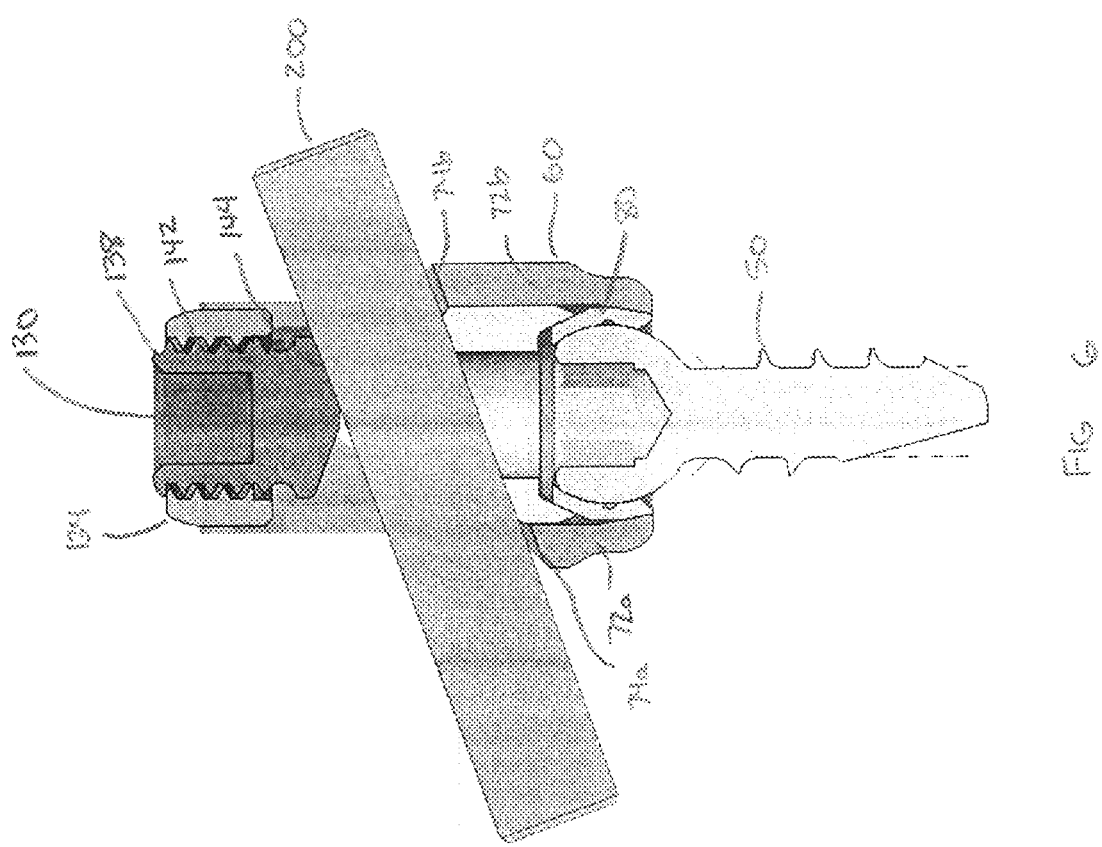
FIG. 6 is a cross-sectional view of a bone screw assembly with locking assembly and implant according to some embodiments.

FIG. 6 is a cross-sectional view of a bone screw assembly with locking assembly and implant according to some embodiments. From this view, additional novel features of the assembly, and in particular, of the locking assembly 130, are visible. As shown in FIG. 6, the bottom of the set screw 138 of the locking assembly 130 includes at least one angled surface 144. The angled surface 144 is configured to contact the surface of the implant 200, thereby providing a downward compressive force. In some embodiments, the angled surface 144 is substantially parallel to the angled surface of the angled wedge member and/or angled slot. In other embodiments, the angled surface 144 is at an angle that is non-parallel relative to the angled surface of the angled wedge member and/or angled slot, but includes at least a portion that is in contact with the implant 200 to apply a compressive force.

Figure 7:
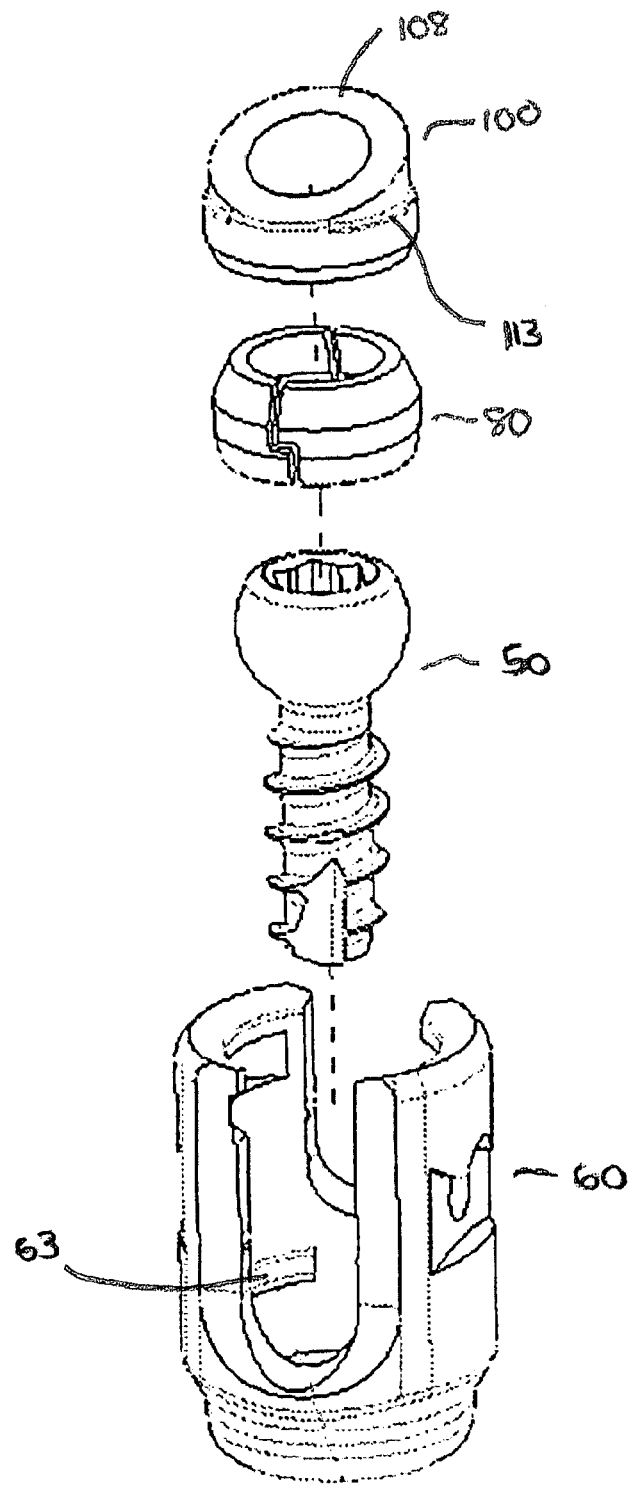
FIG. 7 is an exploded perspective view of a bone screw assembly including an angled wedge member with mating cuts according to some embodiments.

FIG. 7 is an exploded perspective view of a bone screw assembly including an angled wedge member with mating cuts according to some embodiments. Like the bone screw assembly in FIG. 2, the bone screw assembly in FIG. 7 includes a coupling member 60, a screw member 50, a coupling body component 80 and an angled wedge member 100.

In the alternative embodiment, the angled wedge member 100 also includes one or more mating cuts 113 formed on an outer surface. The mating cuts 113 advantageously form an uneven and/or stepped surface that is capable of being retained via one or more radial shoulders 63 placed in the interior of the coupling member 60. In some embodiments, the mating cuts 113 match the features of the radial shoulders 63 and help keep the angled wedge member in a proper orientation within the coupling member.

In the illustrated embodiment in FIG. 7, the radial shoulder 63 extends substantially horizontally (e.g., transverse to an inner surface of the coupling member), which can be desirably manufactured with ease. Advantageously, the bottom of the radial shoulder 63 contacts the mating cuts 113 of the angled wedge member 100 and keeps the wedge member in a proper orientation and position within the coupling member 60.

In alternative embodiments, a bone screw assembly can be provided having a coupling member with an angulated portion. Like previous embodiments, the alternative embodiments advantageously accommodate implants and/or locking assembly components through an incision at a same or substantially similar angle as a screw member, thereby reducing the need to expand the size of an incision during surgery.

Figure 8A:
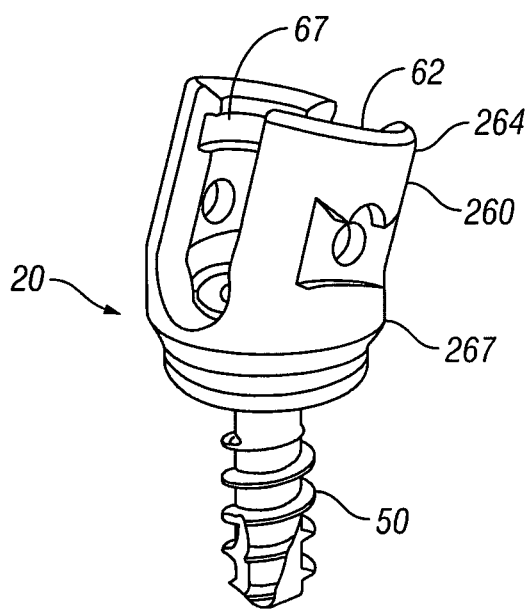
FIG. 8A is a perspective view of another bone screw assembly having a coupling member with an angulated portion according to some embodiments.

FIG. 8A is a perspective view of such an alternative bone screw assembly having a coupling member with an angulated portion. The alternative bone screw assembly 20 includes a coupling member 260 having an angulated top portion 264 that is at an angle relative to a bottom portion 267. The angulated top portion 264 has a longitudinal axis that is different from the longitudinal axis of the bottom portion 267 which runs through the screw member. The angulated top portion 264 of the coupling member includes a pair of extension elements 62 and a pair of recesses or grooves 67 formed in an inner wall for mating with a cap member 134 of a locking assembly 130 (shown in FIG. 8B).

Figure 8B:
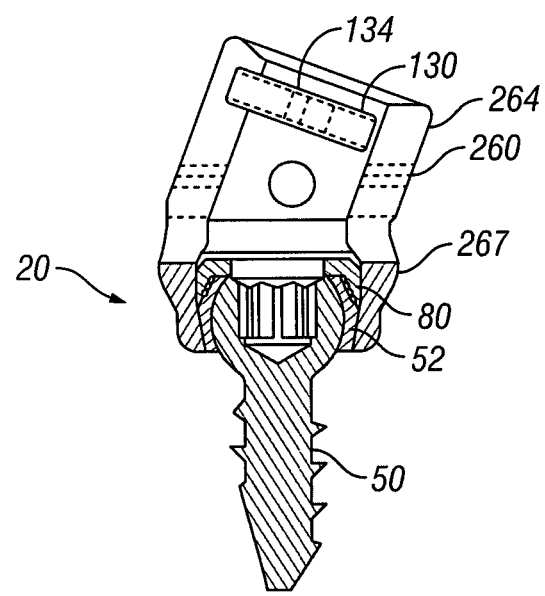
FIG. 8B is a cross-sectional view of the bone screw assembly in FIG. 8A.

FIG. 8B is a cross-sectional view of the bone screw assembly of FIG. 8A. From this view, the interior of the coupling member 260 with angulated top portion 264 is shown with the screw member 50. To secure the screw member 50 within the coupling member 260, a coupling body component 80 having one or more slits can be used, as discussed above. In addition, a locking assembly 130 comprising a cap screw 134 and set screw 138 can be delivered downwardly through the top of the coupling member 260 to assist in securing the screw member within the coupling member 260.

Figure 8C:
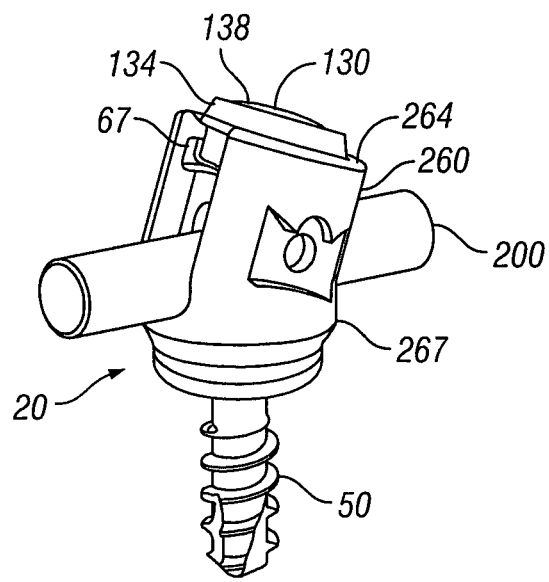
FIG. 8C is perspective view of the bone screw assembly in FIG. 8A with an implant.

FIG. 8C is a perspective view of the bone screw assembly of FIG. 8A with an implant 200 (e.g., a rod member) secured therein. From this view, the locking assembly 130 including cap screw 134 and set screw 138 is visible. Advantageously, due to the angulated top portion 264 of the coupling member 260, the components of the locking assembly 130 can be delivered at the same angle and through the same incision as the screw member 50.

In alternative embodiments, a bone screw assembly can be provided having a bone screw having a head with an off-axis angle relative to the screw body. Advantageously, providing a screw with an off-axis head allows for greater angulation to more easily facilitate surgical procedures.

Figures 9A, 9B:
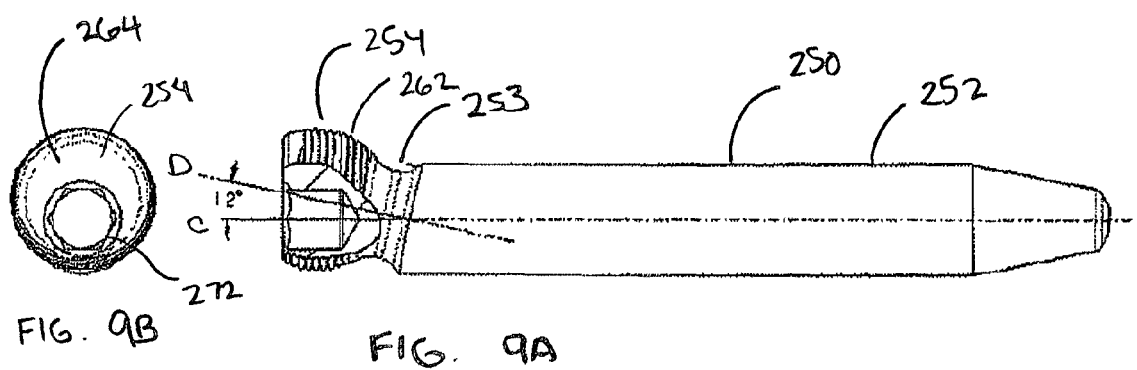
FIG. 9A is a side perspective view of another bone screw assembly having a head with an off-axis angle relative to the screw body according to some embodiments.
FIG. 9B is a top view of the head of the bone screw in FIG. 9A.

FIG. 9A is a side perspective view of a bone screw having a head with an off-axis angle relative to the screw body according to some embodiments. The bone screw 250 includes a body 252, neck 253 and head 254 with threads 262. As shown in FIG. 9A, the body of the screw 252 (which can be threaded) runs along a first longitudinal C-axis, while the neck 253 extends along a second longitudinal D-axis that is different and off-axis from the C-axis. As the off-axis neck 253 transitions into the head 254 of the screw, the head 254 of the screw is also considered to be off-axis relative to the screw body 252. In some embodiments, the degree of off-set between the C-axis and the D-axis (and hence, between the head and/or neck relative to the screw body) is between about 6 and 18 degrees, or about 12 degrees. By having a head and/or neck that is off-axis from the screw body, this advantageously provides for a greater degree of angulation by a coupling member 60 (shown in FIG. 9C) medially, laterally or in any direction relative to the screw member.

As shown in FIG. 9A, each of the components of the bone screw (e.g., body 252, neck 253 and head 254) can be formed as a single monolithic piece. In other embodiments, the components can be formed separately and can be joined together to form a screw with an off-axis head and/or neck.

FIG. 9B is a top view of the head of the bone screw in FIG. 9A. The head 254 of the bone screw includes a top surface 264 with an aperture 272 formed therethrough. The top surface 264 is substantially smooth and flat. The aperture 272, which is used to receive a screw driver (e.g., a hexagonal screw driver) for securing the screw to a bone, has a longitudinal axis that is off-set from the longitudinal axis of the head and/or neck of the screw. Instead, the longitudinal axis through the aperture runs near or substantially along the longitudinal C-axis of the screw body 252, thereby allowing the screw to be properly screwed into a bone member, even with the off-axis head and/or neck.

Figure 9C:
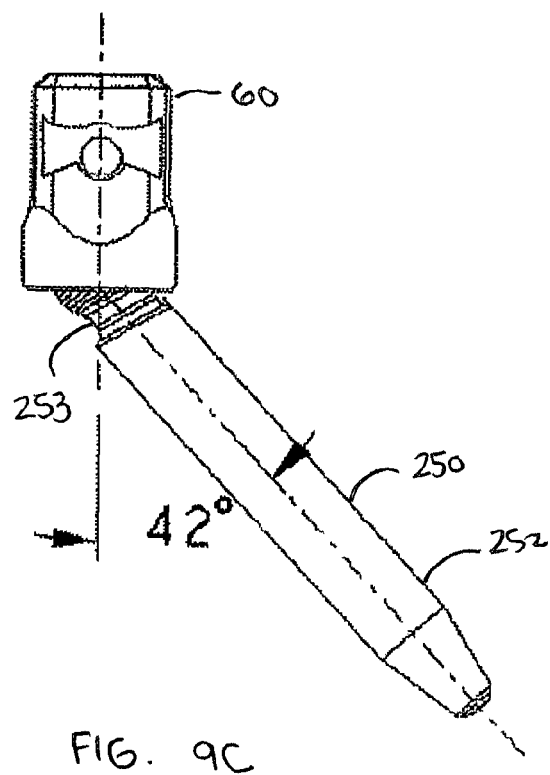
FIG. 9C is a side view of a bone screw assembly including the bone screw in FIG. 9A.

FIG. 9C is a side view of a bone screw assembly including the bone screw in FIG. 9A. The assembly comprises a coupling member 60 and a screw body 250 that is received in the coupling member 60. Advantageously, due to the off-set head and/or neck member, the coupling member 60 has a greater degree of angulation medially or laterally relative to the screw member 250 compared to conventional screw assemblies. In some embodiments, the degree of angulation of the coupling member 60 relative to the screw member 250 is at least about 30 degrees, or at least about 36 degrees, or at least about 42 degrees. In some embodiments, providing a high degree of angulation (e.g., 42 degrees) in a medial direction advantageously allows for stabilizing implants (e.g., rod members) to be side-loaded into the angulated coupling member 60. Thus, the stabilizing implant (e.g., rod member) can be captured with more ease, especially in spondyliosis and/or deformity cases.

Methods of Use

The application encompasses a bone screw assembly for use in implantation of screws in a bone cavity of a subject requiring stabilization or immobilization of one or more bones (e.g., vertebrae).

Specifically, the application encompasses a bone screw assembly including an angled wedge member and/or a coupling member with one or more angled slots that can be used in the human body.

The bone screw assembly of the application can be implanted and used to stabilize different types of bone (e.g., hip, femur, vertebra). The surgical procedures using the improved bone screw assembly can be performed minimally invasively, although the bone screw assembly can also be used in "mini-open" and open surgical procedures for fixation and stabilization.

In some embodiments, the application encompasses methods for treating a subject requiring bone stabilization or fixation comprising:

a. forming an incision in a body of a patient;

b. inserting a first pre-assembled bone screw assembly including a first screw member through the incision at a first angle;

c. attaching the first screw member to a first vertebral body;

d. inserting a second pre-assembled bone screw assembly through the incision at a second angle, the second pre-assembled bone screw assembly including a coupling member having an angled slot, a second screw member, a coupling body component and an angled wedge member;

e. attaching the second screw member to a second vertebral body;

f. delivering a rod implant through the incision and into contact with the angled wedge member of the second pre-assembled bone screw assembly;

g. connecting the rod implant between the first bone screw assembly and the second bone screw assembly; and h. delivering a first locking assembly through the incision to secure the rod implant to the first pre-assembled bone screw assembly and a second locking assembly through the incision to secure the rod implant to the second pre-assembled bone screw assembly to assist in spinal stabilization.

With the assistance of the improved bone screw assembly described herein, it is possible to deliver the multiple surgical components (e.g., screw member, rod implant and locking assembly components) through a single incision with minimal or no expansion of the incision during the surgical procedure. In some embodiments, the incision can therefore be advantageously kept to between about 5 and 130 mm, or between about 10 and 90 mm during the entire surgical procedure. The bone screw assembly can advantageously be used in percutaneous, mini-open or open surgical procedures.

The above described procedure can be performed using a single incision as part of a mini-open procedure. In other embodiments, the procedure can be performed minimally invasively through multiple incisions or stab wounds.

While the procedure described above utilizes a bone screw assembly with an angled wedge member as in FIG. 2, similar procedures can be performed utilizing the bone screw assembly in FIGS. 8A-8C. Similar procedures can also be performed using a screw assembly with an off-axis head member as in FIGS. 9A-9C.

Kits

The application also contemplates kits of various bone screw assemblies of the invention as well as the tools needed for surgery, for example, flexible segment portions or rigid rods for use in spinal surgery. The bone screw assemblies can be manufactured in various widths and sizes to accommodate different types of surgeries and needs of the surgeon.

The kits of the application are intended to broaden a surgeon's options once in surgery to provide a patient with the most optimal stabilization system. In addition to providing surgical options, the addition of the improved bone screw assemblies in one or more kits described herein helps to reduce the amount of overall surgical procedure time by reducing the need to expand an incision during surgery.

It will be apparent to those skilled in the art that various modifications and variations can be made in the present invention without departing from the scope or spirit of the invention. Moreover, the improved bone screw assemblies and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure.

It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone screw assemblies. Thus, it is intended that the present invention cover the modifications and variations of this invention provided that they come within the scope of the appended claims or their equivalents.

What is claimed is:

1. A bone stabilization system comprising:
   a coupling member, wherein the coupling member comprises an upper surface and a lower surface;
   a screw member configured to be received in the coupling member, wherein the screw member is downwardly delivered into the coupling member such that it passes the upper surface the coupling member and moves in a direction from the upper surface to the lower surface of the coupling member;
   a wedge member configured to be received in the coupling member, wherein the wedge member includes a bottom surface and a top surface that is non-parallel to the bottom surface;
   a rod implant configured to be received in the coupling member; and a locking assembly configured to secure the rod implant within the coupling member; and
   a coupling body component having one or more slits to assist in securing the screw member to the coupling member, wherein the coupling body component is independent from the coupling member, wherein the coupling body component is downwardly delivered into the coupling member such that it passes the upper surface of the coupling member and moves in a direction from the upper surface to the lower surface of the coupling member.

2. The bone stabilization system of claim 1, wherein the coupling member includes a pair of extension elements.

3. The bone stabilization system of claim 2, wherein the coupling member includes a pair of angled slots having angled contact surfaces between the extension elements.

4. The bone stabilization system of claim 1, wherein the coupling member includes a bumper element along an inner surface of the coupling member.

5. The bone stabilization system of claim 4, Wherein the bumper element comprises an angled shoulder.

6. The bone stabilization system of claim 1, wherein the bottom surface of the wedge member is substantially horizontal.

7. The bone stabilization system of claim 1, wherein the top surface of the wedge member is at an angle of between about 15 and 30 degrees from the bottom surface.

8. The bone stabilization system of claim 1, wherein the locking assembly includes a cap member and a set screw received therein.

9. The bone stabilization system of claim 8, wherein the set screw includes an angled bottom surface.

10. The bone stabilization system of claim 9, wherein the angled bottom surface of the set screw is substantially parallel to the top surface of the wedge member.

11. A bone stabilization system comprising:
    a coupling member including a pair of extension elements and a pair of angled slots formed therebetween, wherein the angled slots include angled contact surfaces, wherein the coupling member comprises an upper surface and a lower surface;

a screw member configured to be received in the coupling member, wherein the screw member is downwardly delivered into the coupling member such that it passes the upper surface of the coupling member and moves in a direction from the upper surface to the lower surface of the coupling member;

a wedge member configured to be received in the coupling member and positioned on top of the screw member, wherein the wedge member includes a bottom surface and a top surface at a non-parallel angle to the bottom surface;

a rod implant configured to be received in the coupling member and seated on top of the angled contact surfaces; and a locking assembly configured to secure the rod implant within the coupling member; and a coupling body component configured to fit around at least a portion of a head of the screw member, wherein the coupling body component is independent from the coupling member and is downwardly delivered into the coupling member, wherein the coupling body component is downwardly delivered into the coupling member such that it passes the upper surface of the coupling member and moves in a direction from the upper surface to the lower surface of the coupling member.

12. The bone stabilization system of claim 11, wherein the coupling member includes a recessed groove for receiving the wedge member.

13. The bone stabilization system of claim 11, wherein the top surface is at an angle of between about 15 and 30 degrees relative to the bottom surface.

14. The bone stabilization system of claim 11, wherein the locking assembly includes a cap member and a set screw therein.

15. The bone stabilization system of claim 14, wherein the set screw includes an angled bottom surface that is substantially parallel to the angled contact surfaces of the coupling member.

16. A bone stabilization system comprising:

a coupling member including a pair of extension elements, wherein the pair of extension elements form slots, wherein the bottom of the slots include angled contact surfaces for contacting a rod member delivered in the coupling member, wherein the coupling member includes one or more inner bumper elements, and wherein the coupling member comprises an upper surface and a lower surface;

a screw member including a head and a threaded shaft, wherein the screw member is configured to be received in the coupling member, wherein the screw member is downwardly delivered into the coupling member such that it passes the upper surface of the coupling member and moves in a direction from the upper surface to the lower surface of the coupling, member;

a coupling body component, wherein the coupling body component is configured to extend over a portion of the head of the screw member to assist in securing the screw member to the coupling member, wherein the coupling body component is downwardly delivered into the coupling member such that it passes the upper surface of the coupling member and moves in a direction from the upper surface to the lower surface of the coupling member;

an angled wedge member configured to be received in the coupling member on top of the screw member, the angled wedge member including a substantially horizontal bottom surface and an angled top surface that is non--parallel to the bottom surface a rod member receivable in the slots of the coupling member, wherein the rod member is configured to contact the angled top surface of the angled wedge member; and a locking assembly comprising a cap member and a set screw, the set screw having an angled bottom surface that is substantially at the same angle as the angled top surface of the angled wedge member, wherein the locking assembly is configured to be delivered down the coupling member to apply a compressive force that secures the rod member within the coupling member.

\* \* \* \* \*